US00PP20102P3

(12) United States Plant Patent
DeWelt

(10) Patent No.: US PP20,102 P3
(45) Date of Patent: Jun. 16, 2009

(54) ***PAPAVER* SUPER POPPY HYBRID PLANT 'HEARTBEAT'**

(50) Latin Name: *Papaver* hybrid
Varietal Denomination: Heartbeat

(75) Inventor: James Peter DeWelt, Atascadero, CA (US)

(73) Assignee: Sandra M. Worth, Water Meadow, Nursery Cheriton NR Alresford, Hampshire (GB)

( * ) Notice: Subject to any disclaimer, the term of this patent is extended or adjusted under 35 U.S.C. 154(b) by 911 days.

(21) Appl. No.: 10/619,411

(22) Filed: Jul. 16, 2003

(65) Prior Publication Data

US 2005/0015835 P1 Jan. 20, 2005

(51) Int. Cl.
*A01H 5/00* (2006.01)

(52) U.S. Cl. ..... Plt./464
(58) Field of Classification Search ..... Plt./263, Plt./464

See application file for complete search history.

*Primary Examiner*—Kent L Bell

(57) ABSTRACT

The present invention relates to a new and distinct cultivar of *Papaver* plant named 'Heartbeat' characterized by having an upright habit, with thick supporting stems, dark, glossy green foliage, large semi-double purple/maroon flowers, thick, glossy flower petals, that withstand the rigors of ultra-violet rays, rain, and wind and therefore flowers for a long period, and a vigorous growth habit.

3 Drawing Sheets

Genus/species: *Papaver* hybrid.
Variety Denomination: 'Heartbeat'.

BACKGROUND OF THE INVENTION

The present invention relates to a new and distinct *Papaver* super poppy hybrid plant named 'Heartbeat'. The new *Papaver* is a product of a planned breeding on Sep. 25$^{th}$ 1997, by the inventor in Atascadero, in the County of San Louis Obispo Calif. U.S.A. The new *Papaver* is an inter-specific hybrid, originated from a cross pollination of the following *Papaver* species: *Papaver atlanticum, Papaver californicum*, *Papaver rupifragrum, papaver somniferum*, and *Papaver orientale*.

The inventor selected the new *Papaver* in 1998 from the resulting progeny on the basis of its floriferousness, remarkable coloration, and its vigor.

The breeding scheme was *Papaver* hybrid×*Papaver orientale* of an unnamed cultivar. The female, or seed parent, of this sowing being an inter-specific hybrid of the species *Papaver atlanticum, Papaver californicum, Papaver rupifragrum, papaver somniferum*, and *Papaver orientale*. The male, or pollen parent, was an unnamed *Papaver orientale* seedling of unknown parentage. Trials were set up in both Atascadero in the County of San Luis Obispo Calif. U.S.A. from 1998 to 2001 and at the National Collection of *Papaver* U.K. in Cheriton Hampshire England U.K. from 200 to 2002.

Asexual reproduction of the new *Papaver* super poppy hybrid plant 'Heartbeat' was accomplished by cuttings at Atascadero U.S.A. The instant plant has shown that the unique features of this new *Papaver* are stable and reproduces true to type in successive generations of asexual reproduction.

BRIEF SUMMARY OF THE INVENTION

Plants of the *Papaver* super poppy hybrid plant 'Heartbeat' have not been observed in all possible environmental conditions. The phenotype may vary somewhat with variations of the environment such as temperature, light intensity, day length, and fertility level without, however, any variance in genotype.

The following trials have been repeatedly observed and are determined to be the unique characteristics of 'Heartbeat':

1. Upright habit with thick supporting stems.
2. Dark, glossy, green foliage.
3. Large semi double purple/maroon flowers.
4. Thick, glossy flower petals that withstand the rigors of ultra violet rays, rain, and wind.
5. Plants flower for a long period.
6. Vigorous growth habit.

BRIEF DESCRIPTION OF THE DRAWINGS

The accompanying colored photographs illustrate the overall appearance of the new cultivar, showing the colors as true as it is reasonably possible to obtain in colored reproductions of this type. Colors of the photograph may differ slightly from the color values cited in the detailed botanical description which accurately describe the actual colors of the new cultivar. All photographs are of a mature plant (3 years old) of *Papaver* super poppy hybrid 'Heartbeat' grown in garden soil.

Figure 1:
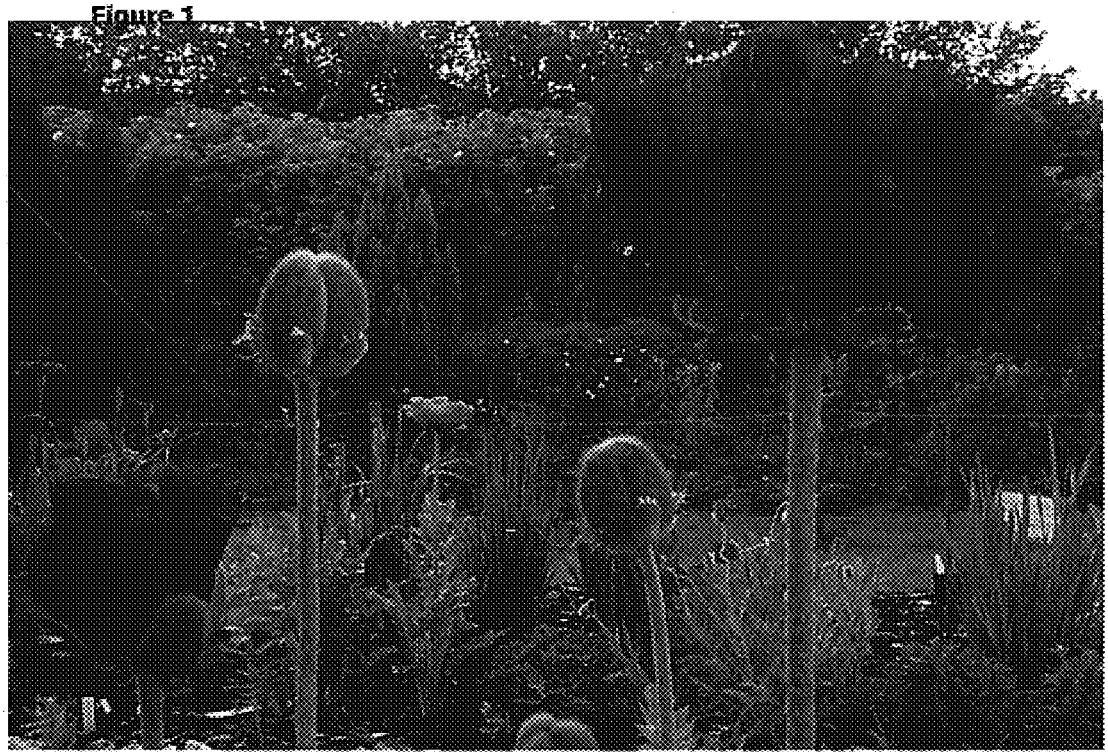
FIG. 1. The top photograph shows buds, stems, bracts, scales, and a side view of an opening flower of 'Heartbeat'. The bottom photograph shows a close-up view of a typical flower of 'Heartbeat'.
Figure 1:
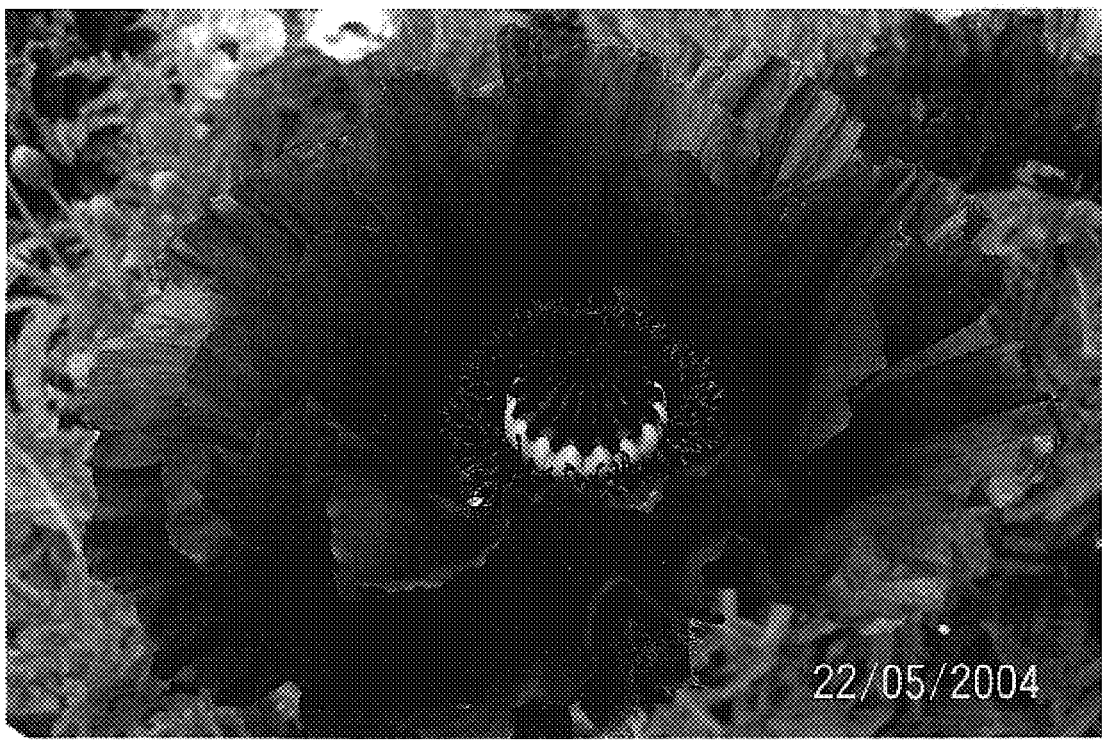
Figure 2:
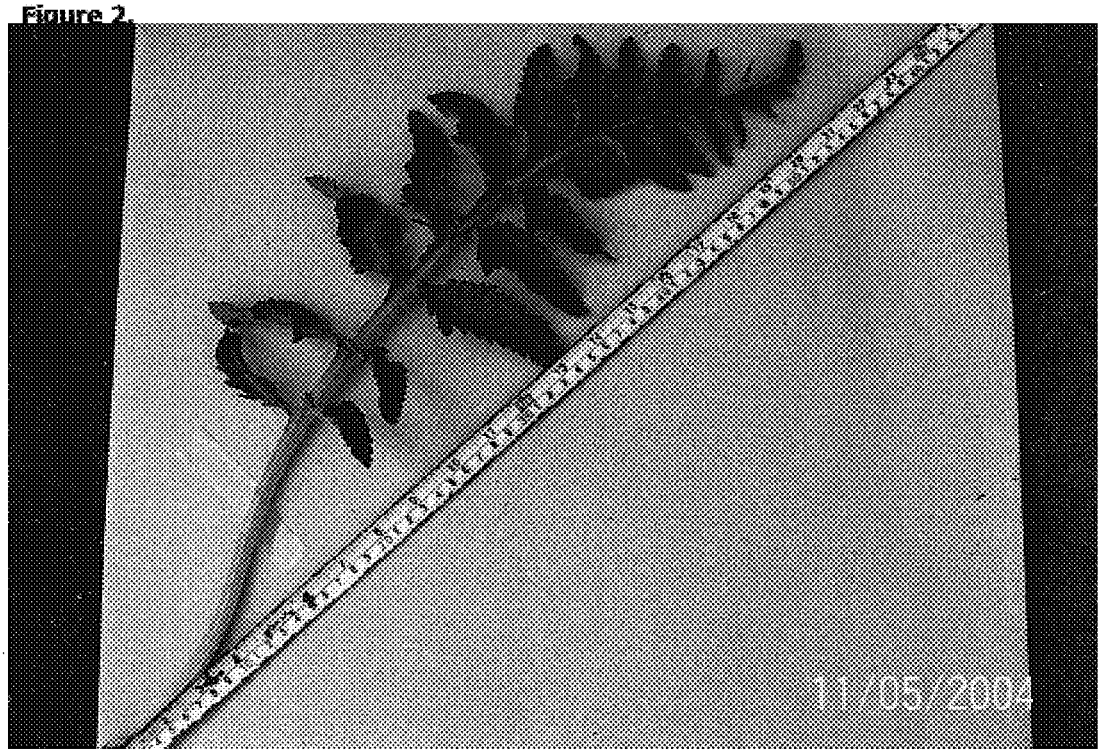
FIG. 2. Top photograph shows a mature leaf of 'Heartbeat'. The bottom photograph shows a close up of a side view of the stem, scales, small bract, black vein lines, and the opened bowl shaped flowers of 'Heartbeat', FIG. 3. This photograph shows three stems, bracts, scales, and seed capsules of 'Heartbeat' placed on the right of the photograph. The left of the photograph shows *Papaver ori-*
Figure 2:
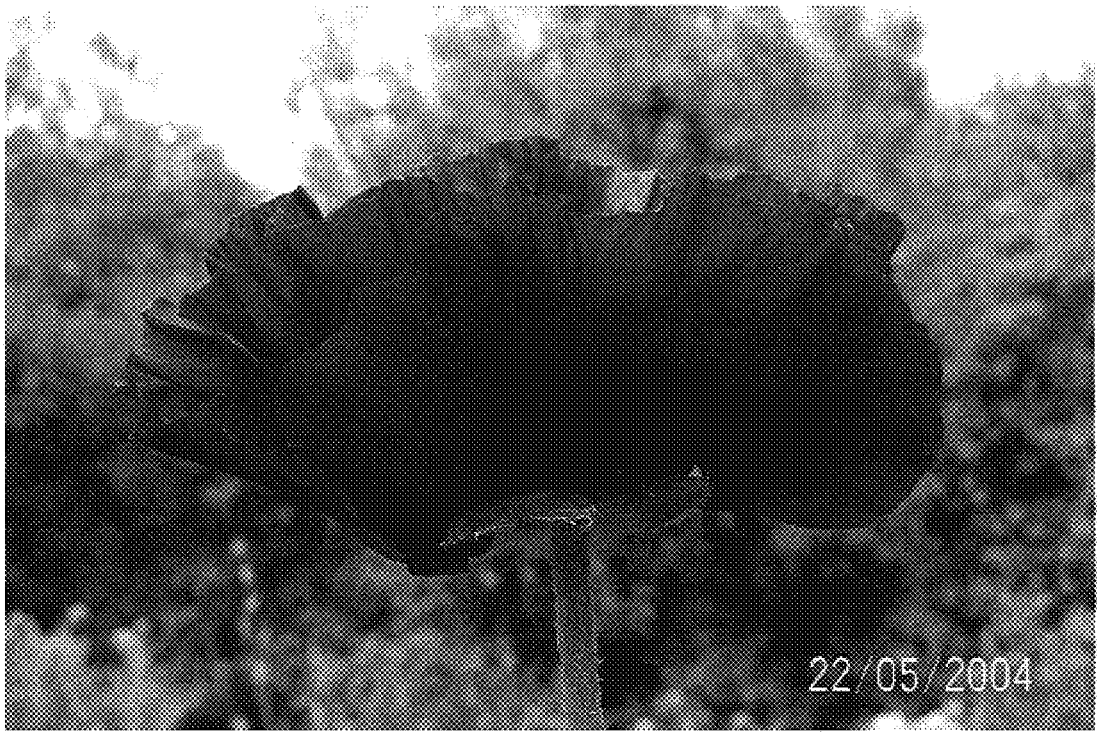

*ental* 'Royal Chocolate Distinction' showing the seed capsule, stem, bracts, and scale.

DETAILED BOTANICAL DESCRIPTION:

In the following description color references are made to The Royal Horticultural Society Colour Chart except where general terms of ordinary dictionary significance are used. Plants used for the description was three years old and classed as mature and grown in garden beds with normal garden soil. 'Heartbeat' is an inter-specific hybrid seedling from a sowing of seed on Sep. 25$^{th}$ 1997 in the City Atascadero, in the County of San Luis Obispo, Calif.

Plant Description:
Form: Robust hispid perennial flowering plant with upright, sturdy, erect, and tall flowering stems, the foliage forming a symmetrical arching circle around the plant.
Plant height: About 36 inches.
Plant diameter: About 24 inches.
Propagation:
Type: Cuttings.
Time to develop roots: Cuttings harvested in October will develop roots in February in the Northern Hemisphere.
Root description: Fleshy.
Crop time: About 20 weeks are required to produce finished flowering plants for a 2 liter container.
Foliage description: Leaves simple, generally symmetrical and long persisting.
Arrangement: Alternate and irregular.
Shape: Lanceolate, pinnately and deeply dissected.
Length: About 20 to 22 inches.
Width: About 7 inches.
Leaf apex: Acuminate to acute.
Leaf base: Attenuate.
Leaf margin: Serrate to Serrulate.
Leaf attachment: Sessile.
Leaf texture: Glossy, slightly rugose; Both upper and lower surfaces covered with pale grey to greenish white hairs between 1/16 inch to 1/8 inch in length.
Young foliage upper surface: 137C.
Young foliage lower surface: 137D.
Mature foliage upper surface: Closest to 137A to 137B, veins 145D.
Mature foliage lower surface: Closest to 137C, veins 144B.
Flower description:
Flower type and Habit: Large size, 6 petals, semi-double flowers circular in shape, set with three outer overlapping petals and three more upright inside petals overlapping, the edges to all petals ruffled and slightly pleated, and one or two petals may have some serrated edges to the margins. Flowers upward and outward facing. Flowers not persistent. Freely flowering typically about 12 flowers and flowering buds at one time.
Natural flowering season: Late spring to early summer.
Rate of opening: About 3 weeks from visible bud to open flower.
Fragrance: Not detected.
Flower longevity on the plant: Average 7 to 8 days before petals drop.
Flower size:
Flower diameter: 5.5 inches to 7.5 inches.
Flower depth: About 3.5 inches.
Bud: (Before showing color) Oblong with domed bulbous top.
Bud color: (Outside surface) 137C with maroon to purple dot 71A.
Length: About 2.25 inches.
Diameter: About 1.25 inches.
Texture: Hispid covered with white, pale green to maroon red hairs about 1/16 inch to 1/8 inch.
Corolla arrangement/appearance: 6 overlapping petals forming a bowl shape, base indented to stem and bracts.
Petal length: About 4 inches.
Petal width: About 6.5 inches.
Petal shape: Orbicular to Reniform.
Petal apex: Obtuse.
Petal base: Truncate to Reniform.
Petal margin: Very fine crenulated edges, one or two petals may have incised margins but this is not constant.
Petal texture: Thick and satin smooth.
Petal color: Deep maroon with purple and slight brown tones.
Petal color upper surface when opening: Red Purple 59A to 59B.
Petal color lower surface when opening: Closest to 59A.
Petal color, base: Black venation lines extending to about 2 inches, over color 59A.
Petal color upper surface when opened: Red Purple 59B with an oblong black blotch above the base.
Petal color lower surface when opened: Closest to 59B.
Petal color lower surface base: Black venation lines extending to about 2 inches, over color 59B.
Peduncle/flowering stems:
Length: About 36 inches.
Diameter: About 1/2 inch.
Strength: Excellent, fully supporting the weight of the flowers, thick, upright, and self supporting.
Texture: Hispid with pale grey to greenish white, horizontal hairs to lower stem and flat hairs to upper part of stem.
Peduncle/stem color: 137D.
Peduncle leaves: Smaller leaves attached to the stem at irregular intervals.
Length of smaller Leaves: Varying from 4.5 inches to 8 inches.
Calyx/sepal arrangement:
Calyx length: About 2.25 inches.
Calyx width: About 1.5 inches.
Sepal number: Typically 3.
Sepal shape: Elliptic.
Sepal apex: Mucronate.
Sepal margin: Entire.
Sepal margin color: 149D.
Sepal color outer surface: Nearest 137C to 137D with maroon to purple dot markings nearest 71A.
Sepal color inner surface: Nearest 149D.
Sepal texture: Hispid, covered with pale greenish to red/purple hairs.
Length of hairs: 1/8 inch 1/4 inch.
Diameter of hairs: Very fine.
Bracts: Irregular, medium to small, with white hirsute edges to apex and margins.
Length: 1.5 inches to 2.5 inches.
Color (upper surface): 137D, veins 143B.
Color (lower surface): 137C, veins 143B.
Scales: Obtuse with white hispid margins and apex. Scales not constant.
Scale color: 137D.
Reproduction organs:
Stamen quantity: Numerous, typically more than 200.
Anther shape: Basifixed.
Anther length: About 3/16 inch.
Anther color: 202A.

Figure 3:
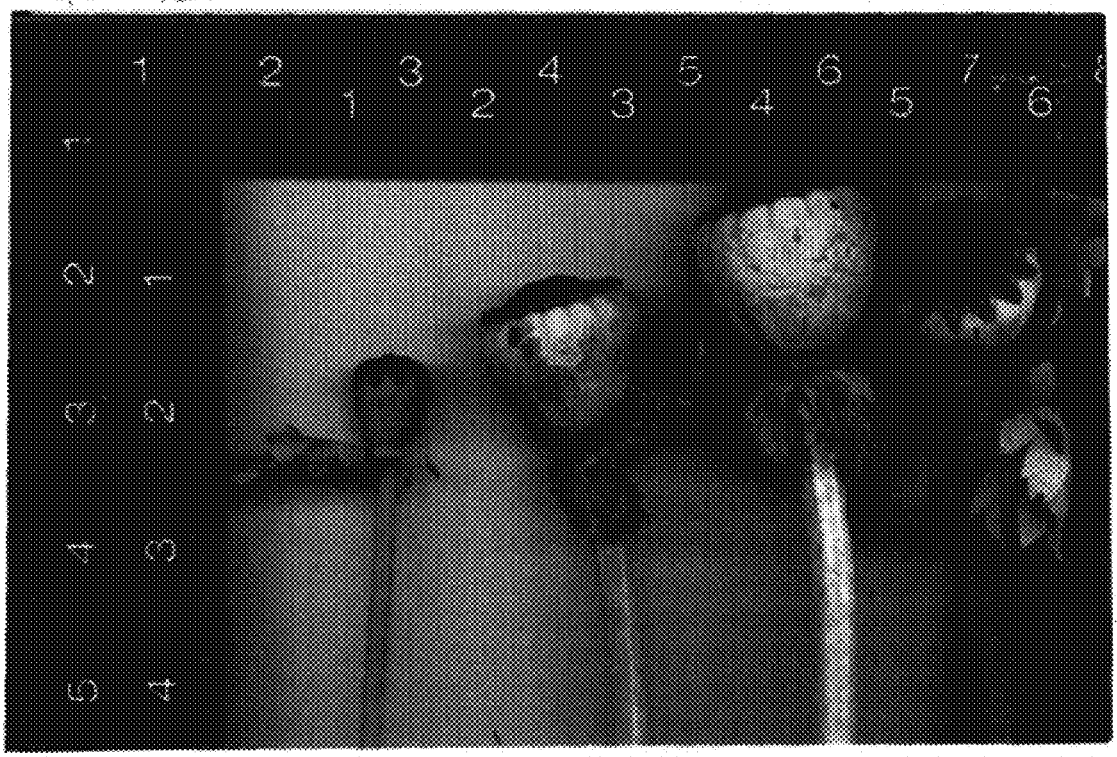

Pollen amount: Scarce.
Pistil quantity: One.
Pistil length: About ⅛ inch.
Stigma color: 200A.
Seed or poricidal capsule: The instant plant has very large, attractive seed capsule adding to the uniqueness, (See FIG. 1., Lower Photograph and FIG. 3.) with pronounced indented markings on the top edge of the pericarp even when unripe and in flower.
Color when in flower: Nearest to 142D.
Length: About 1.5 inches.
Diameter: About 1.25 inches.
Color of seed capsule: 133D.
Seed description:
Length: 1/16 inch.
Diameter: 1/16 inch.
Seed color: Dull dark brown.
Disease resistance: The instant plant has been noted to be free of pathogens common to *Papaver*.
Weather tolerance: The instant plant is tolerant to rain, wind, and U.V. rays.
Comparisons: The instant plant differs from its male parent in the following ways:

1. 'Heartbeat' plants are faster growing than the male parent in all climate zones.
2. 'Heartbeat' plants produce more flowers in total then the male parent.

What is claimed is:

1. A new and distinct *Papaver* plant named 'Heartbeat', as illustrated and described herein.

* * * * *